United States Patent [19]

Taylor et al.

[11] Patent Number: 5,013,738

[45] Date of Patent: May 7, 1991

[54] L-GLUTAMIC ACID DERIVATIVES

[75] Inventors: Edward C. Taylor; Thomas H. Schrader, both of Princeton; Loren D. Walensky, Millburn, all of N.J.

[73] Assignee: The Trustees of Princeton University, Princeton, N.J.

[21] Appl. No.: 510,669

[22] Filed: Apr. 18, 1990

[51] Int. Cl.$^5$ .................. A61K 31/505; C07D 239/36; C07D 239/48
[52] U.S. Cl. ..................................... 514/272; 544/321
[58] Field of Search ..................... 514/272; 544/321

[56] References Cited

U.S. PATENT DOCUMENTS 4,880,812 11/1969 Kelley ................................. 544/321

Primary Examiner—John M. Ford
Attorney, Agent, or Firm—Mathews, Woodbridge & Collins

[57] ABSTRACT

Substituted pyrimidin-5-yl derivatives of L-glutamic acid are anti-neoplastic agents. A typical embodiment is N-{4-[6-(2,6-diamino-4-hydroxypyrimidin-5-yl)hex-1-en-3-yl]benzoyl}-L-glutamic acid.

12 Claims, No Drawings

L-GLUTAMIC ACID DERIVATIVES

This invention pertains to derivatives of L-glutamic acid which are antineoplastic agents, to their preparation and use, and to intermediates useful in their preparation.

BACKGROUND OF THE INVENTION

The folic acid antimetabolites aminopterin and amethopterin (also known as 10-methylaminopterin or methotrexate) are antineoplastic agents. These compounds inhibit enzymatic conversions involving metabolic derivatives of folic acid. Amethopterin, for example, inhibits dihydrofolate reductase, an enzyme necessary for the regeneration of tetrahydrofolate from dihydrofolate which is formed during the conversion of 2-deoxyuridylate to thymidylate by the enzyme thymidylate synthetase.

Other derivatives of folic acid and aminopterin have been synthesized and tested as antimetabolites. Among these are compounds in which a methylene or methylidene group occupies a position in the molecule normally occupied by an imino or nitrilo group respectively. These derivatives have varying degrees of antimetabolic activity. 10-Deazaaminopterin is highly active (Sirotak et al., *Cancer Treat. Rep.* 1978, 62, 1047) and 5-deazaaminopterin has activity similar to that of amethopterin (Taylor et al., *J. Org. Chem.*, 1983, 48, 4852). 8,10-Dideazaaminopterin is reported to be active (U.S. Pat. No. 4,460,591) and 5,8,10-trideazaaminopterin exhibits activity against mouse L1210 leukemia (Yan et al., *J. Heterocycl. Chem.*, 1979, 16, 541). 10-Deazafolic acid, on the other hand, shows no significant activity (Struck et al., *J. Med. Chem.*, 1971, 14, 693) and 5-deazafolic acid is only weakly cytotoxic. 8, 10-Dideazafolic acid is only marginally effective as a dihydrofolate reductase inhibitor (DeGraw et al., "Chemistry and Biology of Pteridines", Elsevier, 1979, 229) and 5,8, 10-trideazafolic acid also shows only marginal activity against mouse L1210 leukemia (Oatis et al., *J Med. Chem.*, 1977, 20, 1393). 5,10-Dideazaaminopterin and 5,10-dideaza-5,6,7,8-tetrahydroaminopterin, and the corresponding 5,10-dideazafolic acid derivatives are reported by Taylor et al., *J. Med. Chem.*, 28:7, 914 (1985).

DETAILED DESCRIPTION

The invention pertains to glutamic acid derivatives of the formula:

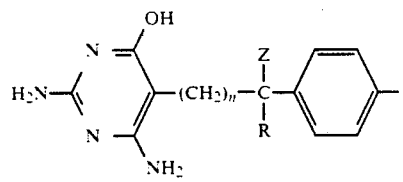
(I)

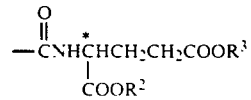

in which
n has a value of 2 to 5;
R is vinyl or hydroxymethyl and Z is hydrogen or R and Z taken together are methylene;
each of $R^2$ and $R^3$ is hydrogen or a carboxylic acid protecting group; and
the configuration about the carbon atom designated * is L; and
the pharmaceutically acceptable salts thereof.

The compounds of Formula I in which each of $R^2$ and $R^3$ is hydrogen, and the salts thereof, are antineoplastic agents; the compounds of Formula I in which each or both of $R^2$ and $R^3$ are carboxylic acid protecting groups are chemical intermediates useful in the preparation of the former compounds.

The compounds of Formula I are shown in the 3,4-dehydro-4-hydroxy form but exist in tautomeric equilibrium with the corresponding 4(3H)-oxo compounds:

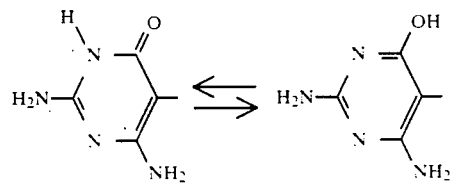

For convenience, the 3,4-dehydro-4-hydroxy form is depicted and the corresponding nomen-clature is used throughout this specification. it being understood that in each case such includes the tautomeric 4(3H)-oxo forms.

The invention includes the pharmaceutically acceptable alkali metal, alkaline earth metal, non-toxic metal, ammonium, and substituted ammonium salts, such as for example the sodium, potassium, lithium, calcium, magnesium, aluminum, zinc, ammonium, trimethylammonium, triethylammonium, triethanolammonium, pyridinium, substituted pyridinium, and the like.

The compounds can be prepared by hydrolysis of a 2,6-diamino-4-hydroxypyrimidin-5-yl-L-glutamic acid derivative of the formula:

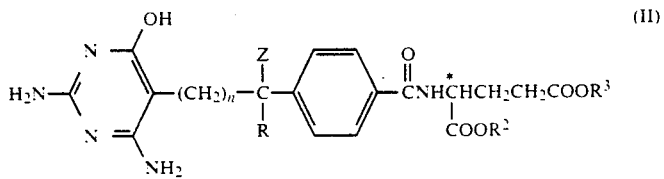
(II)

in which each of $R^2$ and $R^3$ is the same or different carboxylic acid protecting group, and n, Z and R are as defined above.

Protecting groups encompassed by $R^2$ and $R^3$ and reactions for their removal are described, for example, in "Protective Groups in Organic Chemistry", Plenum Press, London and New York (1973); Greene, "Protective Groups in Organic Synthesis", Wiley, New York (1981); "The Peptides", Vol. I, Schroder and Lubke, Academic Press, London and New York (1965); in "Methoden der organischen Chemie", HoubenWeyl, 4th Edition, Vol. 15/I, Georg Thieme Verlag, Stuttgart (1974). Carboxylic acid protecting groups can be, for example, esters conceptually derived from lower alkanols of from 1 to 6 carbon atoms, including those branched in the 1-position and those which are substituted with one of more aromatic groups such as phenyl, or with halo or alkoxy; e.g., methyl, ethyl, t-butyl, benzyl, 4-nitrobenzyl, diphenylmethyl, methoxymethyl, and the like esters. Silyl esters such as trimethylsilyl also can be employed.

The hydrolysis is conducted at normal temperatures utilizing aqueous acid or base, such as for example, an aqueous alkali metal hydroxide, optionally in the presence of a water miscible organic solvent such as methanol, ethanol, tetrahydrofuran, dimethylformamide, and the like, or an acid, as for example triflouroacetic acid. When base is used, the product is initially formed as the dicationic glutamate salt and can be readily precipitated by adjustment of pH, as through acidification with, for example, acetic acid. The resulting products generally are crystalline or microcrystalline solids.

Compounds of Formula II can be prepared by coupling a compound of the formula:

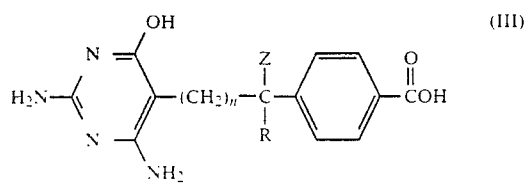

with a protected glutamic acid derivative of the formula

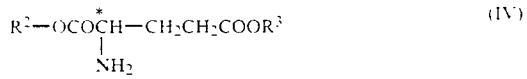

utilizing conventional condensation techniques for the formation of peptide bonds, such as activation of the carboxylic acid group through formation of a mixed anhydride, treatment with DCC, or the use of diphenylchlorophosphonate.

Formation of the intermediate of Formula III can be accomplished by cyclization of an α-cyano dicarboxylate of the formual

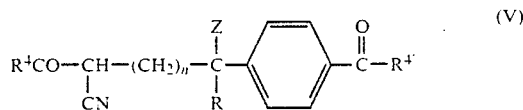

in which $R^4$ and $R^{4'}$ are the same or different alkoxy group of 1 to 6 carbon atoms and n, Z and R are as herein defined, with guanidine free base. Following formation of the pyrimidine ring, the $R^{4'}$ group can be removed through hydrolysis.

The intermediates of Formula V can be prepared by condensing an alkyl cyanoacetate of the formula:

with an ester of the formula:

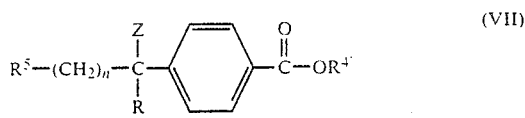

in which n, Z, R, $R^4$ and $R^{4'}$ are as herein defined and $R^5$ is halogen in the presence of a strong base such as sodium hydride.

The ester intermediates of Formula VII are either known or can be prepared by known methods, as more fully exemplified below.

Typical compounds of the present invention include N-(4-[5-(2,6-diamino-4-hydroxypyrimidin-5-yl)pent-1-en-2-yl]benzoyl)-L-glutamic acid; N-(4-[6-(2,6-diamino-4-hydroxypyrimidin-5-yl)hex-1-en-3-yl]benzoyl)-L-glutamic acid; and N-(4-[1-hydroxy-5-(2,6-diamino-4-hydroxypyrimidin-5-yl)pent-2-yl]benzoyl)-L-glutamic acid.

The compounds of Formula I contain a chiral center in the L-glutamic acid portion of the molecule. If no other chiral centers are present, the compounds are obtained in this configuration as the single enantiomer. If Z is hydrogen, however, a second chiral center is present, leading to diastereomers. These diastereomers can be separated mechanically, as by chromatography, so that each is in a form substantially free of the other; i.e., having an optical purity of >95%. Alternatively, a mixture of diastereoisomeric compounds of Formula I is treated with a chiral acid operable to form a salt therewith. The resultant diastereoisomeric salts are then separated through one or more fractional crystallizations and thereafter the free base of the cationic moiety of at least one of the separated salts is liberated through treatment with a base and removal of the protecting groups. The liberation of the cation of the salt can be performed as a discrete step before or after the removal of the protecting groups, or concomitantly with the removal when such groups are susceptible to removal under basic conditions; i.e., basic hydrolysis.

Suitable chiral acids include the individual enantiomers of 10-camphorsulfonic acid, camphoric acid, alpha bromocamphoric acid, methoxyacetic acid, tartaric acid, diacetyltartaric acid, malic acid, pyrrolidone-5-carboxylic acid, and the like.

The compounds of this invention have an effect on one or more enzymes which utilize folic acid, and in particular metabolic derivatives of folic acid, as a substrate. For example, the $IC_{50}$ in whole cell human leukemia cell lines, CCFR-CEM, of N-(4-[5-(2,6-diamino-4-hydroxypyrimidin-5-yl) pent-1-en-2-ylbenzoyl)-L-glutamic acid is approximately 0.004 μg/ml, while that for N-(4-[6-(2,6-diamino-4-hydroxypyrimidin-5-yl)-hex-1-en-3-yl]benzoyl)-L-glutamic acid is approximately 0.0035 μg/ml.

Cytotoxicity is reversed by addition of purines such as hypoxanthine or by addition of leucovorin or aminoimidazolecarboxamide (AICA) but is not reversed by addition of thymidine, indicating specific inhibition in the de novo purine synthesis.

The compounds of Formula I can be used, alone or in combination, to treat neoplasms including choriocarcinoma, leukemia, adenocarcinoma of the female breast, epidermid cancers of the head and neck, squamous or small-cell lung cancer, and various lymphosarcomas. The compounds can also be used to treat mycosis fungoides, psoriasis, and arthritis. The compounds can be administered either orally or preferably parenterally, alone or in combination with other anti-neoplastic agents, steroids, etc., to a mammal suffering from neoplasm and in need of treatment. Parenteral routes of administration include intramuscular, intrathecal, intravenous, or intraarterial. In general, the compounds are administered in much the same fashion as methotrexate, but because of a different mode of action, can be administered in higher dosages than those usually employed with methotrexate. Dosage regimens must be titrated to the particular neoplasm, the condition of the patient, and the response but generally doses will be from about 10 to about 100 mg/day for 5-10 days or single daily administration of 250-500 mg., repeated periodically; e.g. every 14 days. Oral dosage forms include tablets and capsules containing from 1-10 mg of drug per unit dosage. Isotonic saline solutions containing 20-100 mg/ml can be used for parenteral administration.

The following examples will serve to further illustrate the invention.

EXAMPLE 1

N-(4-[6-(2,6-Diamino-4-hydroxypyrimidin-5-yl)hex-1-en-3-yl]benzoyl)-L-glutamic acid

A. 2-(4-Allyphenyl)-4,4-dimethyl-2-oxazoline

This compound was prepared according to Meyers et al., *J. Org. Chem.*, 1974, 39:2787. High purity magnesium (>99.99%) and doubly distilled anhydrous tetrahydrofuran were used for the preparation of the Grignard reagent. The reaction mixture was hydrolyzed with saturated ammonium chloride solution and extracted three times with ether. The extracts were dried over magnesium sulfate and the solvent evaporated under reduced pressure to yield the intermediate which was further purified by flash chromatography eluting with 1:5 ethyl acetate:hexanes. $^1$H NMR (CDCl$_3$, 300 MHz): $\delta$=1.40 (s, 6H, (CH$_3$)$_2$); 3.39 (d, 2H, CH$_2$—C=, J=7.5 Hz); 4.05 (s, 2H, CH$_2$O); 5.05 (d, 1H$_{olef}$, CH(H)=CH, J$_{trans}$=16 Hz); 5.10 (d, 1H$_{olef}$, CH(H)=CH, J$_{cis}$=10 Hz); 5.92 (ddt, 1H$_{olef}$, CH=CH$_2$, J=7.5, 10, 16 Hz); 7.22 (d, 2H$_{arom}$, J=9 Hz); 7.88 (d, 2H$_{arom}$, J=9 Hz).

B. 2-[4-(6-Bromohex-1-en-3-yl)phenyl]-4,4-dimethyloxazoline

A 2 liter three neck round-bottomed flask equipped with a rubber septum, a reflux condenser, and a dropping addition funnel, was torched dry, cooled to room temperature, and charged with 20.6 ml (14.88g, 2.1 eq) of diisopropylamine in 800 ml of anhydrous tetrahydrofuran under a nitrogen atmosphere. After cooling the mixture to 0° C. in an ice bath, 56 ml of n-butyllithium (2.5M, 2.0 eq) were added dropwise. The mixture was stirred for 15 minutes, and then heated in an oil bath at 45° C. A solution of 15.0 g (1.0 eq) of 2-(4-allyphenyl)-4,4-dimethyl-2-oxazoline in 200 ml of anhydrous tetrahydrofuran was adding dropwise to the mixture over a 2 minute period and the reaction mixture then was stirred for 5 to 6 minutes at 45° C. One hundred and fifteen milliliters (16 eq) of 1,3-dibromopropane were quickly added with vigorously stirring and the reaction mixture then was stirred at 45° C. for 45 minutes. One hundred milliliters of saturated ammonium chloride solution were added, followed by extraction with diethyl ether. The extracts were dried over magnesium sulfate and concentrated under reduced pressure to yield the product which was further purified by distillation under vacuum (30° C., 0.1 mm) to remove excess 1,3-dibromopropane and flash chromatography, eluting with 1:5 ethylacetate:hexanes. M.S.: m/z=335.0890 (M$^+$, calc. for C$_{17}$H$_{22}$NO$^{79}$Br: 335.0884), 322, 320 (100%), 265, 214. $^1$H-NMR(CDCl$_3$, 300 MHz):$\delta$=1.39 (s, 6H, (CH$_3$)$_2$); 1.7-2.0(m, 4H, CH$_2$—CH$_2$); 3.32 (dt, 1H, CH—C, J=7.5 Hz); 3.40 (t, 2H, CH$_2$—Br, J=7.5 Hz); 4.12 (s, 2H, CH$_2$O); 5.06 (d, 1H$_{olef}$, CH(H)=CH, J$_{trans}$=18 Hz); 5.08 (d, 1H$_{olef}$, CH(H)=CH, J$_{cis}$=10 Hz); 5.95 (ddd, 1H$_{olef}$, CH=CH$_2$, J=7.5, 10, 18 Hz); 7.23 (d, 2H$_{arom}$, J=9 Hz); 7.91 (d, 2H$_{arom}$, J=9 Hz).

C. Ethyl 4-(6-bromohex-1-en-3-yl) benzoate

The procedure of Meyers et al. supra. was followed for the alcoholysis of the compound produced in step B above. Thirteen grams (1 eq) of 2-[4-(6-bromohex-1-en-3-yl)phenyl]4,4-dimethyloxazoline were dissolved in a mixture of 910 ml of ethanol, 50 ml of water, and 40 ml of concentrated sulfuric acid. The mixture was refluxed for 20 hours. After cooling to approximately 40° C., most of the ethanol was removed under reduced pressure. The residue was extracted with diethyl ether three times, and the combined extracts dried over magnesium sulfate and evaporated to yield the product which was further purified by flash chromatography, eluting with 1:15 ethylacetate:hexanes. M.S.: m/z=310.0578 (M$^+$, calc. for : C$_{15}$H$_{19}$O$_2^{79}$Br: 310.0568), 267, 265, 239, 237, 204, 189, 145, 117 (100%). I.R. (NaCl): $\nu$=2910, 1710(s), 1610, 1365, 1270 (s), 1180, 1100 (s), 1015, 910, 760 cm$^{-1}$. $^1$H-N.M.R.(CDCl$_3$, 300 MHz):$\delta$=1.43 (t, 3H, CH$_3$—CH$_2$O, J=7.5 Hz); 1.7-2.0(m, 4H, CH$_2$—CH$_2$); 3.37 (dt, 1H, CH—CH=, J=7.5 Hz); 3.42 (t, 2H, CH$_2$—Br, J=7.5 Hz); 4.39 (q, 2H, CH$_3$—CH$_2$O, J=7.5 Hz); 5.09 (d, 1H$_{olef}$, CH(H)=CH, J$_{trans}$=18 Hz); 5.11 (d, 1H$_{olef}$, CH(H)=CH, J$_{cis}$=9 Hz); 5.94 (ddd, 1H$_{olef}$, CH=CH$_2$, J=7.5, 9, 18 Hz); 7.28 (d, 2H$_{arom}$, J=9 Hz); 8.00 (d, 2H$_{arom}$, J=9 Hz).

D. Ethyl 4-(7-Carboethoxy-7-cyano-hept-1-en-3-yl)benzoate

A 1 liter three neck round-bottomed flask, equipped with a reflux condenser, additional funnel, and gas inlet, was charged with 1.45 g (5 eq) of 80% sodium hydride (1.16 g of 100% NaH) in 400 ml of anhydrous tetrahydrofuran. This mixture was cooled to 0° C. and 6.15 ml (6 eq) of an anhydrous tetrahydrofuran solution of ethylcyanoacetate were added dropwise under a nitrogen atmosphere. The mixture was vigorously stirred and allowed to attain room temperature until the evolution of hydrogen ceased (approximately 30 minutes). A solution of 3.00 grams (1 eq) of ethyl 4-(6-bromohex-1-en3-yl) benzoate in 50 ml of anhydrous tetrahydrofuran was added and the mixture then refluxed for 36 hours. Saturated ammonium chloride was added and the mixture then extracted three times with diethyl ether. The combined organic extracts were dried over magnesium sulfate and concentrated under reduced pressure to yield the product which was further purified by flash chromatography eluting with 1:3 ethyl acetate:hexanes. M.S.: m/z=343.1778 (M$^-$, calc. for C$_{20}$H$_{25}$NO$_4$: 343.1783), 297 (100%), 270, 189, 145, 117. I.R. (NaCl): $\nu$=2970, 2925, 2860, 2240 (w, CN), 1740 (s), 1715 (s), 1610, 1450, 1405, 1370, 1270 (s), 1180, 1105, 1020, 920, 855, 770 710 cm$^{-1}$. $^1$H-N.M.R. (CDCl$_3$, 300 MHz): $\delta$=1.32 (dt, 3H, CH$_3$—CH$_2$O$_2$C—CH—CN, J=7.5 Hz); 1.41 (t, 3H, CH$_3$—CH$_2$O$_2$C—Ar, J=7.5 Hz); 1.4-1.68 (m, 2H, CH$_2$—CH$_2$—CH$_2$); 1.78 (m, 2H, CH$_2$—CH—CH=); 1.97 (dt, 2H, CH$_2$—CH—CN, J=7.5 Hz); 3.33 (dt, 1H, CH—C≡, J=7.5 Hz); 3.47(dt, 1H, CH—CN, J=7.5 Hz); 4.27 (dq, 2H, CH$_3$—CH$_2$OC—CH*, J=7.5 Hz); 4.38 (q, 2H, CH$_3$—CH$_2$O$_2$C—Ar, J=7.5 Hz); 5.08 (d, 1H$_{olef.}$, CH(H)=CH, J$_{trans}$=18 Hz); 5.12 (d, 1H$_{olef.}$, CH(H)=CH, J$_{cis}$=10 Hz); 5.92 (dd, 1H$_{olef.}$, CH=CH$_2$, J=7.5, 10, 18 Hz); 7.26 (d, 2H$_{arom.}$, J=9 Hz); 8.01 (d, 2H$_{arom.}$, J=9 Hz).

E. Ethyl 4-[6-(2.6-diamino-4-hydroxypyrimidin-5-yl)hex-1-en-3-yl] benzoate

Sodium metal (460 mg, 2 eq) was completely dissolved in 10.0 ml of anhydrous ethanol and 1.05 g (1.1 eq) of dry guanidine hydrochloride was added. The mixture was stirred for 30 minutes at ambient temperature. The solid was removed by filtration and the filtrate transferred to a 50 ml round-bottomed flask equipped with a reflux condenser and a gas inlet. A mixture of ethyl 4-(7-carboethoxy-7-cyanohept-1-en-3-yl)benzoate (3.4 g, 1.0 eq) in 10 ml of anhydrous ethanol was added to the filtrate and the mixture refluxed for 12 hours under a nitrogen atmosphere. The solution was cooled to ambient temperature and 0.6 ml (1 eq) of glacial acetic acid were added. The solvent was removed under reduced pressure to yield the product which was further purified by flash chromatography eluting with 10:1 chloroform:methanol. m.p. 184° C.; M.S.: m/z=356.1853 (M+, calc. for C$_{19}$H$_{24}$N$_4$O$_3$: 356.1848), 311, 167, 152, 139 (100%). 1H-N.M.R. (DMSO-d$^6$, 300 MHz): δ=1.03–1.23 (m, 2H, CH$_2$—CH$_2$—CH$_2$); 1.28 (t, 3H, CH$_3$CH$_2$O, J=7.5 Hz); 1.64 (m, 2H, CH$_2$—CH—CH=); 2.13 (t, 2H, CH$_2$-pyr, J=7.5 Hz); 3.36 (dt, 1H, CH—C≡, J=7.5 Hz); 4.27 (q, 2H, CH$_3$CH$_2$O, J=7.5 Hz); 4.98 (d, 1H$_{olef.}$, CH(H)=CH, J$_{cis}$=10 Hz); 5.00 (d, 1H$_{olef.}$, CH(H)=CH, J$_{trans}$=19 Hz); 5.60 (s (broad), 2H, NH$_2$); 5.80 (s (broad), 2H, NH$_2$); 5.92 (ddd, 1H$_{olef.}$, CH=CH$_2$, J=7.5, 10, 19 Hz); 7.32 (d, 2H$_{arom.}$, J=8 Hz); 7.85 (d, 2H$_{arom.}$, J=8 Hz); 9.73 (s (broad), 1H, NH).

F. 4-[6-(2,6-Diamino-4-hydroxypyrimidin-5-yl)hex-1-en-3-yl]benzoic Acid

A 50 ml round bottomed flask was charged with 1.35 g (1 eq) of ethyl 4-[6-(2,6-diamino-4-hydroxypyrimidin-5-yl)-hex-1-en-3-yl] benzoate, as prepared in step E, in 19 ml of 1N aqueous sodium hydroxide (approximately 5 eq). The mixture was heated at 60° C. for 1 hour and then continuously stirred overnight at room temperature. Impurities were removed by filtration and the filtrate was mixed with 1.6 ml of glacial acetic acid to precipitate the product. The precipitate was centrifuged with water, collected, dissolved in methanol, and concentrated under reduced pressure. m.p. 210° C. M.S.: m/z=328.1531 (M+, calc. for C$_{17}$H$_{20}$N$_4$O$_3$: 328.1535). 1H-N.M.R. (DMSO-d$^6$, 300 MHz): 1.03–1.35 (m, 2H, CH$_2$—CH$_2$—CH$_2$); 1.66 (m, 2H, CH$_2$—CH—CH=); 2.17 (t, 2H, CH$_2$-pyr, J=7.5 Hz); 3.34 (dt, 1H, CH—C≡, J=7.5 Hz); 4.98 (d, 1H$_{olef.}$, CH(H)=CH, J$_{cis}$=10 Hz); 5.00 (d, 1H$_{olef.}$, CH(H)=CH, J$_{trans}$=19 Hz); 5.67 (s (broad), 2H, NH$_2$); 5.91 (ddd, 1Holef., CH=CH$_2$, J=7.5, 10, 19 Hz); 5.98 (s (broad), 2H, NH$_2$); 7.31 (d, 2H$_{arom.}$, J=8 Hz); 7.85 (d, 2H$_{arom.}$, J=8 Hz); 10.02 (s (broad), 1H, NH).

G. Dimethyl N-{4-[6-(2,6-Diamino-4-hydroxypyrimidin-5-yl)-hex-1-en-3-yl]benzoyl}-L-glutamate A solution containing 950 mg eq) of 4-[6-(2,6-diamino-4-hydroxypyrimidin-5-yl)hex-1-en-3-yl]benzoic acid as prepared in step F, 351 mg (1.2 eq) Of N-methylmorpholine, and 10.0 ml of anhydrous dimethylformamide, was vigorously stirred at ambient temperature for 5 minutes. To this solution was added 556 mg (1.1 eq) of 2,4-dimethoxy-6-chloro-1,3,5-triazine and this mixture was then stirred at room temperature for 40 minutes. Following addition to the solution of 351 mg (1.3 eq) of N-methylmorpholine, and 795 mg (1.3 eq) of dry dimethyl-L-glutamate hydrochloride, the mixture was continuously stirred overnight at room temperature and the solvent then removed under reduced pressure. The product was dissolved in chloroform, and extracted with saturated aqueous sodium bicarbonate to remove unreacted acid, triazine and triazinone. The organic extract was dried over magnesium sulfate, filtered and evaporated to dryness to yield the product which was further purified by flash chromatography eluting with 1:10 methanol:chloroform. M.S. m/z=485.2269 (M+, calc. for C$_{24}$H$_{31}$N$_5$O$_6$: 485.2274). 1H-N.M.R. (CDCl$_3$, 300 MHz): 1.03–1.35 (m, 2H, CH$_2$—CH$_2$CH$_2$); 1.62 (m, 2H, CH$_2$—CH—CH=); 2.15 (t, 2H, CH$_2$-pyr, J=7.5 Hz); 2.0–2.5 (m, 4H, 2×CH$_{2(glu)}$); 3.18 (m, 1H, CH—C≡); 3.56 (s, 3H, CH$_3$O); 3.66 (s, 3H, CH$_3$O); 4.70 (m, 1H, CH$_{glu}$); 4.8–5.0 (m, 2H$_{olef.}$); 4.89 (s (broad), 2H, NH$_2$); 5.6–5.9 (m, 3H, NH$_2$+CH=CH$_2$); 7.08 (d, 2H$_{arom.}$, J=8 Hz); 7.50 (m, 1H, NH$_{glu}$); 7.63 (d, 2H$_{arom.}$, J=8 Hz); 11.25 (s (broad), 1H, NH$_{pyr}$).

H. N-(6-[4-(2,6-diamino-4-hydroxypyrimidin-5-yl)-hex-1-en-3-yl]benzoyl)-L-glutamic Acid A solution consisting of 120 mg of dimethyl N-{4-[6-(2,6-diamino-4-hydroxypyrimidin-5-yl)-hex-1-en-3-yl]benzoyl}L-glutamate in 1.0 ml of 1N aqueous sodium hydroxide (1 eq), was stirred overnight at room temperature to form the disodium salt of N-(6-[4-(2,6-diamino-4-hydroxypyrimidin-5-yl)-hex-1-en-3-yl] benzoyl)-L-glutamic acid. This solution then was vigorously stirred while 0.12 ml (2 eq) of glacial acetic acid was dropwise added tp pH=4.0. The product was collected by filtration, washed three times with 1 ml of cold water, and dried under high vacuum. M.S. (F.A.B.): m/z=458.20261 (M+ +H, calc. for C$_{22}$H$_{28}$N$_5$O$_6$: 458.2039). 1H-N M.R. (DMSO-d$_6$, 300 MHz); δ=1.05–1.40 (m, 2H, CH$_2$—CH$_2$—CH$_2$); 1.64 (m, 2H, CH$_2$—CH—CH=); 1.9–2.25 (m, 2H, CH$_2$—CH$_{glu}$); 2.16 (t, 2H, CH$_2$-pyr, J=7.5 Hz); 2.35 (t, 2H, CH$_2$—CO$_2$H, J=7.5 Hz); 3.34 (dt, 1H, CH—C≡, J=7.5 Hz); 4.35 (dt, 1H, CH$_{glu}$, J=7.5 Hz); 4.97 (d, 1H$_{olef.}$, CH(H)=CH, J$_{cis}$=10 Hz); 5.02 (d, 1H$_{olef.}$, CH(H)=CH, J$_{trans}$=19 Hz); 5.63 (s (broad), 2H, NH$_2$); 5.95 (ddd, 1H$_{olef.}$, CH=CH$_2$, J=7.5, 10, 19 Hz); 5.92 (s (broad), 2H NH$_2$); 7.28 (d, 2H$_{arom.}$, J=8 Hz); 7.82 (d, 2H$_{arom.}$, J=8 Hz); 8.50 (d, 1H, NH$_{glu}$, J=7.5 Hz); 9.81 (s (broad), 1H, NH$_{pyr}$), 12.56 (s (broad), 2H, 2 ×CO$_2$H).

EXAMPLE 2

N-(4-[5-(2,6-Diamino-4-hydroxypyrimidin-5-yl)pent-1-en-2-yl]benzoyl)L-glutamic Acid

A. Methyl 4-(4-Hydroxy-1-butynyl]benzoate

This compound was prepared according to Taylor et al., Heterocycles, 1989, 28:1169, modified by stirring for 3 days at room temperature, extracting with diethyl ether, and filtering over silica gel with 1:1 ethylacetate:hexanes.

B. Methyl 4-(4-Acetoxy-1-oxobutyl)benzoate

To 10.0 g (1 eq) of methyl 4-(4-hydroxy-1-butynyl)-benzoate in 200 ml of 90% aqueous acetic acid and 2.4 g (0.15 eq) of mercuric acetate were added 1.0 ml of concentrated sulfuric acid. The mixture was refluxed for 2 hours at approximately 140° C., and cooled to room temperature to facilitate precipitation of mercury salts. The precipitated mercury salts were removed by filtration and the filtrate extracted three times with dichloromethane. The acidic extract was neutralized to pH 7 with solid sodium bicarbonate and the aqueous layer then extracted with dichloromethane. The extracts were dried over magnesium sulfate and evaporated under reduced pressure to yield the product which was further purified by flash chromatography eluting with 1:2 ethylacetate:hexanes. m.p. 61–62° C. M.S.: m/z=264 ($M^+$, CI), 233.0812 ($M^+$—$CH_3O$, calc. for $C_{13}H_{13}O_5$: 233.0814), 204 ($M^+$-AcOH), 176, 163 (100%), 143. $^1$H-N.M.R. ($CDCl_3$, 300 MHz): $\delta$=2.08 (s, 3H, $CH_3$—CO); 2.10 (quin, 2H, $CH_2$—$CH_2$—$CH_2$, J=7.5 Hz); 3.12 (t, 2H, $CH_2$—CO, J=7.5 Hz); 3.96 (s, 3H, $CH_3O$); 4.20 (t, 2H, $CH_2O$, J=7.5 Hz); 8.02 (d, 2$H_{arom.}$, J=9 Hz); 8.18 (d, 2$H_{arom.}$, J=9 Hz).

C. Methyl 4-(5-Acetoxy-pent-1-en-2-yl)benzoate

Methyl triphenylphosphonium (1.5 g, 1.1 eq) was suspended in 50 ml of anhydrous tetrahydrofuran and 4.0 ml of 1.0M solution of sodium hexamethyldisilazide (1.05 eq) in tetrahydrofuran were added via syringe. The mixture was stirred at room temperature for one hour and a solution of 1.0 g (1.0 eq) of methyl 4-(4-acetoxy-1-oxobutyl)benzoate in anhydrous tetrahydrofuran, was added dropwise. The resulting reaction mixture was stirred for 2 hours at room temperature. Sodium bromide/triphenylphosphineoxide precipitate was removed by filtration, and the filtrate washed with water. After extraction of the aqueous layer with diethyl ether, the organic layers were dried over magnesium sulfate and evaporated to dryness to yield the product which was further purified by flash chromatography eluting with 1:5 ethyl acetate:hexanes. M.S.:m/z=262 ($M^+$,CI), 231.1020 ($M^+$—$CH_3O$, calc. for $C_{14}H_{15}O_3$: 231.1021), 202 ($M^+$- AcOH), 176, 143 (100%). $^1$H-N.M.R. ($CDCl_3$, 300 MHz): $\delta$=1.80(quin, 2H, $CH_2$—$CH_2$—$CH_2$, J=7.5 Hz); 2:04(s, 3H, $CH_3$—CO); 2.62 (t, 2H, $CH_2$—C=, J=7.5 Hz); 3.94(s, 3H, $CH_3O$); 4.10(t, 2H, $CH_2O$, J=7.5 Hz); 5.20 (s, 1$H_{olef.}$); 5.41(s, 1$H_{olef.}$); 7.48(d, 2$H_{arom.}$, J=9 Hz); 8.01(d, 2$H_{arom.}$, J=9 Hz).

D. Methyl 4-(5-Hydroxypent-1-en-2-yl)benzoate

To a solution containing 0.52 g (1.0 eq) of dry potassium carbonate in 100 ml of anhydrous methanol was added 1.0 g (1.0 eq) of methyl 4-(5-acetoxy-pent-1-en-2-yl)benzoate in anhydrous methanol. The resulting reaction mixture was stirred for two hours at room temperature, neutralized by the addition of 7.6 ml of 1N hydrochloric acid (2.0 eq), and extracted twice with dichloromethane. The extracts were dried over magnesium sulfate, and concentrated under reduced pressure to yield the product. mp. 28–30° C. M.S.:m/z= 220.1094, ($M^+$calc. for $C_{13}H_{16}O_3$: 220.1099), 189 ($M^+$—$CH_3$)), 176 (100%), 145. $^1$H-N M.R.($CDCl_3$, 300 MHz): $\delta$=1.56(s (broad), 1H, OH); 1.75(quin, 2H, $CH_2$—$CH_2$—$CH_2$, J=7.5 Hz); 2.60(t, 2H, $CH_2$—C=, J=7.5 Hz); 3.68(t, broad), 2H, $CH_2OH$, J=7.5 Hz); 3.94(s, 3H, $CH_3O$); 5.20(s, 1$H_{olef.}$); 5.42(s, 1$H_{olef.}$); 7.48 (d, 2$H_{arom.}$, J=9 Hz); 8.00(d, 2$H_{arom.}$, J=9 Hz).

E. Methyl 4-(5-Methylsulfonyloxy-pent-1-en-2-yl)benzoate

To a solution of 0.40 g (1.0 eq) of methyl 4-(5-hydroxypent-1-en-2-yl)benzoate and 0.38 g (2.0 eq) of triethylamine in anhydrous diethylether, cooled to 0° C., was added in a dropwise fashion a solution of 0.44 g (2.0 eq) mesitylchloride in anhydrous diethylether. Cooling was discontinued after 15 minutes and the mixture allowed to attain room temperature while stirring under nitrogen for 4 hours. The triethylamine hydrochloride precipitate was extracted with saturated ammonium chloride solution and the aqueous layer then washed three times with diethylether. The combined organic layers were dried over magnesium sulfate and concentrated under reduced pressure to yield the product. M.S.:m/z=298 ($M^-$), 267.0683 ($M^-$—$CH_3O$, calc. for $C_{13}H_{15}O_4S$: 267.0691), 202 ($M^+$—$CH_3$—$SO_3H$), 143 (100%). I.R. (NaCl): $\nu$=2950, 1720, 1610, 1440, 1350, 1280, 1180, 1120, 970, 840, 790, 730 $cm^{-1}$. $^1$H-N.M.R.($CDCl_3$, 300 MHz): $\delta$=1.92 (quin, 2H, $CH_2$—$CH_2$—$CH_2$, J=7.5 Hz); 2.70(t, 2H, $CH_2$—C=, J=7.5 Hz); 3.02(s, 3H, $CH_3$—$SO_3$); 3.96 (s, 3H, $CH_3O$); 4.24(t, 2H, $CH_2O$, J=7.5 Hz); 5.22(s, 1$H_{olef.}$); 5.44 (s, 1$H_{olef.}$); 7.48 (d, 2$H_{arom.}$, J=9 Hz); 8.01(d, 2$H_{arom.}$, J=9 Hz).

F. Methyl 4-(6-Carboethoxy-6-cyanohex-1-en-2-yl)benzoate

A 1 liter three neck round bottomed-flask was equipped with a reflux condenser, addition funnel, and gas inlet, and charged with a mixture of 0.10 g (5.0 eq) of 80% sodium hydride in 40 ml of anhydrous tetrahydrofuran. This mixture was cooled to 0° C. and a solution of 0.39 ml (5.5 eq) of ethyl cyanoacetate in anhydrous tetrahydrofuran was added dropwise under a nitrogen atmosphere. The mixture was vigorously stirred and allowed to attain room temperature until hydrogen evolution was no longer observed. To the mixture was then added 0.40 g (1.0 eq) of methyl 4-(5-methylsulfonyloxy-pent-1-en-2-yl)benzoate in 5 ml of anhydrous tetrahydrofuran. The mixture was then refluxed for 15 hours, saturated ammonium chloride solution was added, and the solution extracted three times with diethylether. The extracts were dried over magnesium sulfate, and concentrated under reduced pressure to give the product (containing some unreacted ethyl cyanoacetate which can be removed by Kugelrohr distillation at 40° C./1 mm Hg). Further purification of the product was accomplished by flash chromatography, eluting with 1:3 ethylacetate:hexanes. M.S.:m/z=315.1458 ($M^-$, calc. for $C_{18}H_{21}O_4N$: 315.1470), 284 ($M^+$—$CH_3O$), 202 ($M^-$—$EtO_2C$—$CH_2$—CN), 176, 143 (100%). $^1$H-N M.R.($CDCl_3$, 300 MHz): $\delta$=1.28(t, 3H, $CH_3$—$CH_2O$, J=7.5 Hz); 1.64(quin, 2H, $CH_2$—$CH_2$—$CH_2$, J=7.5 Hz); 1.96(dt, 2H, CH$_2$—CH, J=7.5 Hz); 2.60(t, 2H, CH$_2$—C≡, J=7.5Hz); 3.44(t, 1H, CH—CN, J=7.5 Hz); 3.92(s, 3H, CH$_3$O); 4.22(q, 2H, CH$_3$—CH$_2$O, J=7.5 Hz); 5.19(s, 1H$_{olef}$); 5.41(s, 1H$_{olef}$); 7.42(d, 2H$_{arom.}$, J=9 Hz); 8.00(d, 2H$_{arom.}$, J=9 Hz).

G. Methyl 5-[4-(2,6-diamino-4-hydroxypyrimidin-5-yl)pent-1-en-2-yl]benzoate

To a solution of sodium metal (190 mg, 2 eq) in 10.0 ml of anhydrous methanol is added 0.414 g (1.1 eq) of dry guanidine hydrochloride. The reaction mixture was stirred at room temperature for about 30 minutes. Sodium chloride precipitate was removed by filtration and the filtrate solution transferred to a 50 ml round-bottomed flask which was equipped with a reflux condenser and a gas inlet. A mixture of 1.30 g (1.0 eq) of methyl 4-(6-carboethoxy-6-cyanohex-1-en-2-yl)benzoate in 10ml of anhydrous methanol is added to the filtrateand the solution then refluxed for 12 hours under a nitrogen atmosphere. After cooling to room temperature, 0.23 ml (1 eq) of glacial acetic acid was added to neutralize excess sodium methoxide. Concentration under reduced pressure yielded the product which was removed by filtration, washed with a cold mixture of 1:1 chloroform:methanol, and dried. M.S.:m/z=328.1530 (M$^+$, calc. for C$_{17}$H$_{20}$N$_4$O$_3$: 328.1535). $^1$H-N.M.R.(DMSO-d$^6$, 300 MHz):δ=1.40(quin, 2H, CH$_2$—CH$_2$—CH$_2$, J=7.5 Hz); 2.25(t, 2H, CH$_2$-pyr, J=7.5 Hz); 2.60 (t, 2H, CH$_2$—C≡, J=7.5 Hz); 3.84(s, 3H, CH$_3$O); 5.10(s, 1H$_{olef}$); 5.36(s, 1H$_{olef}$); 5.62(s (broad), 2H, NH$_2$); 5.93 (s (broad), 2H, NH$_2$); 7.53 (d, 2H$_{arom.}$, J=9 Hz); 7.84 (d, 2H$_{arom.}$, J=9 Hz); 9.86 (s (broad), 1H, NH).

H. 4-[5-(2,6-Diamino-4-hydroxyoyrimidin-5-yl)-pent-1-en-2-yl]benzoic acid

A 50 ml round-bottomed flask was charged with a mixture of 0.420 g (1eq) of methyl 5-[4-(2,6-diamino-4-hydroxypyrimidin-5-yl)-pent-1-en-2-yl]benzoate in 7 ml of 1N of aqueous sodium hydroxide (approximately 5 eq). After heating the solution to 60° C. for 1 hr, the solution was allowed to cool to ambient temperature and then stirred overnight. Impuities were removed by filtration and the filtrate was acidified with 0.35 ml of glacial acetic acid. The resulting solid was collected by centrifugation with water and dissolved in methanol. The solution was concentrated under reduced pressure to give the product. M.S.:m/z=314.1366 (M$^-$, calc. for C$_{16}$H$_{18}$N$_4$O$_3$: 314.1379). $^1$H-N.M.R.(DMSO-d$^6$, 300 MHz): δ=1.40 (quin, 2H, CH$_2$—CH$_2$—CH$_2$, J=7.5 Hz); 2.22(t, 2H, CH$_2$-pyr, J=7.5 Hz); 2.56(t, 2H, CH$_2$—C≡, J=7.5 Hz); 5.14(s, 1H$_{olef}$); 5.39(s, 1H$_{olef}$); 5.68 (s (broad), 2H, NH$_2$); 5.92 (s(broad), 2H, NH$_2$); 7.53(d, 2H$_{arom.}$, J=9 Hz) 7.88 (d, 2H$_{arom.}$, J=9 Hz); 9.82 (s (broad), 1H, NH).

I. Dimethyl N-{4-[5-(2,6-Diamino-4-hydroxypyrimidin-5-yl)-pent-1-en-2-yl]benzoyl}-L-glutamate A mixture of 270 mg (1 eq) of 4-[5-(2,6-diamino-4-hydroxypyrimidin-5-yl)-pent-1-en-2-yl]benzoic acid and 104 mg (1.2 eq) of N-methylmorpholine in 4.0 ml of anhydrous tetrahydrofuran, was vigorously stirred for 5 minutes at room temperature. To this mixture, 165 mg (1.1 eq) of 2,4-dimethoxy-6-chloro-1,3,5-triazine were added and the sol was stirred for 40 minutes at room temperature. An additional 104 mg (1.2 eq) of N-methylmorpholine were introduced followed by 236 mg (1.3 eq) of dry dimethyl-L-glutamate hydrochloride. The solution then was continuously stirred for 4 hours at room temperature. The solvent was removed under reduced pressure and the residue dissolved in chloroform. Extraction with saturated aqueous sodium bicarbonate removed unreacted acid, triazine and triazinone. The organic layer was dried over magnesium sulfate, filtered and evaporated to dryness to yield the product which was further purified by flash chromatography eluting with 1:10 methanol:chloroform. M.S.:m/z=471.2081 (M$^+$, calc. for C$_{23}$H$_{29}$N$_5$O$_6$: 471.2118). $^1$H-N.M.R. (CDCl$_3$, 300 MHz): 1.41(quin, 2H, CH$_2$—CH$_2$—CH$_2$, J=7.5 Hz); 2.00-2.55(m, 8H, 4×—CH$_2$—); 3.56(s, 3H, CH$_3$O); 3.68(s, 3H, CH$_3$O); 4.68 (dt, 1H, CH, J=6, 7.5 Hz); 4.84 (s (broad), 2H, NH$_2$); 4.97 (s, 1H$_{olef}$); 5.18 (s, 1H$_{olef}$); 5.86 (s (broad), 2H, NH$_2$); 7.29 (d, 2H$_{arom.}$, J=9 Hz); 7.62 (m, (broad), 1H, NH$_{glu}$); 7.64 (d, 2H$_{arom.}$, J=9 Hz); 11.20 (s (broad), 1H, NH$_{pyr}$).

J. N-(4-[5-(2,6-Diamino-4-hydroxypyrimidin-5-yl)-pent1-en-2-yl]benzoyl)-L-glutamic acid A solution containing 100mg of dimethyl N-{4-[5-(2,6-diamino-4-hydroxypyrimidin-5-yl)-pent-1-en-2-yl]benzoyl}-L-glutamate in 1.0 ml of 1N aqueous sodium hydroxide was stirred overnight at room temperature to yield the disodium salt of N-{4-[5-(2,6-diamino-4-hydroxypyrimidin-5-yl)-pent 1-en-2-yl]benzoyl}-L-glutamic acid. Glacial acetic acid (0.12 ml, 2 eq) then was added dropwise with vigorous stirring. The desired product was removed by filtration and washed three times with 1 ml of cold water, followed by drying under high vacuum. M.S.(F.A.B.):m/z=444.18695 (M$^-$+H, calc. for C$_{21}$H$_{26}$N$_5$O$_6$: 444.1883). $^1$H-N.M.R. (DMSO-d$_6$, 300 MHz): δ=1.43 (quin, 2H, CH$_2$—CH$_2$—CH$_2$, J=7.5 Hz); 1.85-2.15 (m, 2H, CH$_2$—CH, J=7.5 Hz); 2.21 (t, 2H, CH$_2$-pyr, J=7.5 Hz); 2.36 (dt, 2H, CH$_2$—CO$_2$H, J=7.5 Hz); 2.56 (t, 2H, CH$_2$C—C≡, J=7.5 Hz); 4.36 (dt, 1H, CH, J=6, 7.5 Hz); 5.15 (s, 1H$_{olef.}$); 5.39 (s, 1H$_{olef.}$); 5.69 (s (broad), 2H, NH$_2$); 5.96 (s (broad), 2H, NH$_2$); 7.47 (d, 2H$_{arom.}$, J=9 Hz); 7.83 (d, 2H$_{arom.}$, J=9 Hz); 8.57 (d, 1H, NH$_{glu}$, J=6 Hz); 9.84 (s (broad), 1H, NH$_{pyr}$); 12.65 (s (broad), 2H, 2×CO$_2$H).

EXAMPLE 3

A. Dimethyl N-{4-[1-Hydroxy-5-(2,6-diamino-4-hydroxypyrimidin-5-yl)pent-2-yl]benzoyl)-L-glutamate A 50 ml round bottomed flask equipped with a gas inlet was dried and charged with 500 mg (1 eq) of N-(4-[5-(2,6-diamino-4-hydroxypyrimidin-5-yl)-pent-1-en-2-yl]benzoyl)-L-glutamic acid in 10 ml of anhydrous tetrahydrofuran. To this reaction mixture, 9.0 ml (9.0 eq) of 1.0M borohydride tetrahydofuran etherate was added at a rate of 3 ml/hour and a temperature of 55° C. After vigorously stirring the mixture for three additional hours, the mixture was cooled to room temperature and 200 mg (1 eq) of sodium boroatetrahydrate in 10 ml of water was added. The mixture then was stirred at room temperature for two hours, followed by concentration under reduced pressure to yield the product which was further purified by flash chromatography, eluting with 1:4 methanol/chloroform. m.p. 104° C.

M.S.: m/z=489.2233 (M+, calc. for $C_{23}H_{31}N_5O_7$: 489.2233); $^1$H-NMR (MeOD, 300 MHz): δ=1.22-1.37 (m, 2H, $CH_2$—$CH_2$—$CH_2$); 1.55-1.85 (m, 2H, $CH_2$—$CH_2$—$CH_2$); 2.04-2.35 (m, 2H, $CH_2CH_{glu}$); 2.25 (t, 2H, $CH_2$-pyr, J=7.5 Hz); 2.48 (t, 2H, $CH_2CO_2Me$, J=7.5 Hz); 2.75-2.87 (m, 1H, CH—$CH_2OH$); 3.63 (s, 3H, $CH_3O$); 3.66 (d, 2H, $CH_2OH$, J=7.5 Hz); 3.74 (s, 3H, $CH_3O$); 4.62 (dt, 1H, $CH_{glu}$, J=6, 7.5 Hz); 7.30 (d, 2H$_{arom.}$, J=9 Hz); 7.76 (d, 2H$_{arom.}$, J=9 Hz).

B.

N-{4-[1-Hydroxy-5-2,6-diamino-4-hydroxypyrimidin-5-yl)pent-2-yl]benzoyl}-L-glutamic acid Dimethyl N-{4-[1-hydroxy-5-(2,6-diamino-4-hydroxypyrimidin-5-yl)-pent-2-yl]benzoyl}-L-glutamate (60 mg) was dissolved in 0.5 ml of 1N aqueous sodium hydroxide (1 eq) and the solution then vigorously stirred for one hour at room temperature to yield the disodium salt of N-{4-[1-hydroxy-5-(2,6-diamino-4-hydroxypyrimidin-5-yl)-pent-2-yl]benzoyl}-L-glutamic acid. To this solution, 0.06 ml (2.0 eq) of glacial acetic acid was added dropwise followed by cooling at −10° C. for 30 minutes. The solid was removed by filtration, washed with 1 ml of ice water, and dried to produce N-{4-[1-hydroxy-5-(2,6-diamino-4-hydroxypyrimidin-5-yl)pent-2-yl]benzoyl}-L-glutamic acid, m.p. 164° C. The product contains 1 equivalent of sodium acetate) M.S. (F.A.B.) m/z=(M+ +H, calc. for $C_{21}H_{27}N_5O_7$: 462.1989). $^1$H-NMR (DMSO-d$_6$, 270 MHz): δ=24-1.35 (m, 2H, $CH_2$—$CH_2$—$CH_2$); 1.55-1.95 (m, 2H, $CH_2$—$CH_2$—$CH_2$); 1.98-2.20 (m, 2H, $CH_2$—CH$_{glu}$); 2.25 (t, 2H, $CH_2$—pyr, J=7.5 Hz); 2.47 (dt, 2H, $CH_2$—$CO_2H$, J=7.5 Hz); 2.80-2.90 (m, 1H, CH—$CH_2OH$, J=7.5 Hz); 4.51 (dt, 1H, $CH_{glu}$, J=6, 7.5 Hz); 5.70 (s (broad), 2H, $NH_2$); 6.08 (s (broad), 2H, $NH_2$); 7.42 (d, 2H$_{arom.}$, J=9 Hz); 7.90 (d, 2H$_{arom.}$, J=9 Hz); 8.50 (d, 1H, NH$_{glu}$, J=6 Hz); 9.95 (s (broad), 1H, NH$_{pyr}$); 12.6 (s (broad), 2H, 2×$CO_2H$).

What is claimed is:

1. A compound of the formula

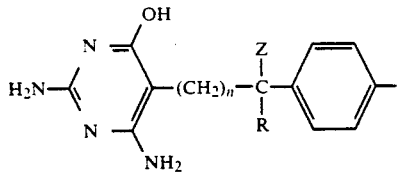

(I)

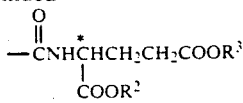

in which n has a value of 2 to 5;

R is vinyl or hydroxymethyl and Z is hydrogen or R and Z taken together are methylene;

each of $R^2$ and $R^3$ is hydrogen or a carboxylic acid protecting group; and the configuration about the carbon atom designated * is L; and the pharmaceutically acceptable salts thereof.

2. A compound according to claim 1 in which each of $R^2$ and $R^3$ is hydrogen.

3. A compound according to claim 2 in which n has a value of 3.

4. A compound according to claim 3 which is N-{4-[6-(2,6-di-amino-4-hydroxypyrimidin-5-yl)hex-1-en-3-yl]benzoyl}-L-glutamic acid.

5. A compound according to claim 3 which is N-{4-[5-(2,6-di-amino-4-hydroxypyrimidin-5-yl)pent-1-en-2-yl]benzoyl}-L-glutamic acid.

6. A compound according to claim 3 which is N-{4-[1-hydroxy-5-(2,6-diamino-4-hydroxypyrimidin-5-yl)pent-2yl]benzoyl}L-glutamic acid.

7. A compound according to claim 1 in which at least one of $R^2$ and $R^3$ is other than hydrogen.

8. A compound according to claim 7 which is dimethyl N-{4-[6-(2,6-diamino-4-hydroxypyrimidin-5-yl)hex-1-en-3-yl]benzoyl}L-glutamate.

9. A compound according to claim 7 which is dimethyl N-{4-[5-(2,6-diamino-4-hydroxypyrimidin-5-yl)pent-1-en-2-yl]benzoyl}L-glutamate.

10. A compound according to claim 7 which is dimethyl N-{4-[1-hydroxy-5-(2,6-diamino-4-hydroxypyrimidin-5-yl)pent-2-yl]benzoyl}L-glutamate.

11. A pharmaceutical composition for combating neoplastic growth in a mammal which comprises an amount of a compound according to claim 2 which upon administration to the mammal in a single or multiple dose regimen is effective to combat said growth, in combination with a pharmaceutically acceptable carrier.

12. A method for combating neoplastic growth in a mammal which comprises administering to the mammal in a single or multiple dose regimen an effective amount of a compound according to claim 2.

* * * * *